(12) United States Patent
Amir

(10) Patent No.: US 9,903,813 B2
(45) Date of Patent: Feb. 27, 2018

(54) OVERLAY MEASUREMENT OF PITCH WALK IN MULTIPLY PATTERNED TARGETS

(71) Applicant: KLA-TENCOR CORPORATION, Milpitas, CA (US)

(72) Inventor: Nuriel Amir, St. Yokne'am (IL)

(73) Assignee: KLA-Tencor Corporation, Milpitas, CA (US)

( * ) Notice: Subject to any disclaimer, the term of this patent is extended or adjusted under 35 U.S.C. 154(b) by 101 days.

(21) Appl. No.: 14/734,687

(22) Filed: Jun. 9, 2015

(65) Prior Publication Data

US 2015/0268164 A1    Sep. 24, 2015

Related U.S. Application Data

(63) Continuation of application No. PCT/US2015/011488, filed on Jan. 14, 2015.

(Continued)

(51) Int. Cl.

| | |
|---|---|
| *G01N 21/00* | (2006.01) |
| *B05D 5/00* | (2006.01) |
| *G01N 21/47* | (2006.01) |
| *B05D 1/32* | (2006.01) |
| *G01N 21/01* | (2006.01) |
| *G03F 7/20* | (2006.01) |

(52) U.S. Cl.
CPC ........... *G01N 21/4785* (2013.01); *B05D 1/32* (2013.01); *G01N 21/01* (2013.01); *G03F 7/70466* (2013.01); *G03F 7/70633* (2013.01)

(58) Field of Classification Search
CPC ...... B05D 1/32; G01N 21/01; G01N 21/4785; G03F 7/70466; G03F 7/70633

USPC ............................ 356/243.1, 237.5; 427/282
See application file for complete search history.

(56) References Cited

U.S. PATENT DOCUMENTS

| | | |
|---|---|---|
| 7,531,449 B2 | 5/2009 | Park et al. |
| 7,557,921 B1 | 7/2009 | Adel et al. |

(Continued)

OTHER PUBLICATIONS

William H. Arnold; "Towards 3nm overlay and critical dimension uniformity: an integrated error budget for double patterning lithography"; ASML Technology Development Center, 8555 S River Parkway, Tempe, AZ 85048; Optical Microlithography XXI, edited by Harry J. Levinson, Mircea V. Dusa; Proc. of SPIE vol. 6924, 692404, 2008.

(Continued)

*Primary Examiner* — Sunghee Y Gray
(74) *Attorney, Agent, or Firm* — Suiter Swantz pc llo

(57) ABSTRACT

Multiply patterned metrology targets and target design methods are provided to enable pitch walk measurements using overlay measurements. Multiply patterned structures having single features or spacers produced simultaneously and sharing a common pitch with the paired features or spacers are used to express pitch walk as a measurable overlay between the structures. For example, targets are provided which comprise a first multiply patterned structure having a single left-hand feature or spacer produced simultaneously and sharing a common pitch with the respective paired features or spacers, and a second multiply patterned structure having a single right-hand feature or spacer produced simultaneously and sharing a common pitch with the respective paired features or spacers.

22 Claims, 9 Drawing Sheets

Related U.S. Application Data

(60) Provisional application No. 61/927,753, filed on Jan. 15, 2014, provisional application No. 62/052,877, filed on Sep. 19, 2014.

(56) References Cited

U.S. PATENT DOCUMENTS

| | | |
|---|---|---|
| 7,615,496 B2 | 11/2009 | Lee et al. |
| 8,232,212 B2 | 7/2012 | Davis et al. |
| 8,293,656 B2 | 10/2012 | Kim et al. |
| 8,664,077 B2 | 3/2014 | Nair et al. |
| 2010/0290285 A1 | 11/2010 | Lee et al. |
| 2012/0043646 A1 | 2/2012 | Kim |
| 2012/0267528 A1 | 10/2012 | Sakai et al. |
| 2012/0292502 A1* | 11/2012 | Langer ............... G01N 23/2251 250/307 |
| 2013/0065397 A1 | 3/2013 | Chen |
| 2013/0208279 A1 | 8/2013 | Smith |
| 2013/0222795 A1 | 8/2013 | Madsen et al. |
| 2013/0318485 A1* | 11/2013 | Park .................... G06F 17/5081 716/102 |
| 2014/0036243 A1 | 2/2014 | Beyer et al. |
| 2014/0073137 A1 | 3/2014 | Cinnor et al. |
| 2014/0193974 A1 | 7/2014 | Lee et al. |

OTHER PUBLICATIONS

Ryoung-Han Kim et al.; "Spacer defined double patterning for sub-72 nm pitch logic technology"; Optical Microlithography XXIII, edited by Mircea V. Dusa, Will Conley; San Jose, California; Proc. of SPIE vol. 7640, 76400F, 2010.

Jo Finders et al; "Double patterning for 32nm and below: an update"; Optical Microlithography XXI, edited by Harry J. Levinson, Mircea V. Dusa; ASML, De Run 1110, 5503 LA Veldhoven, The Netherlands; ASML US Inc, 4211 Burton Dr. Santa Clara, CA, USA; IMEC vzw, Kapeldreef 75, B-3001 Heverlee, Belgium; Proc. of SPIE vol. 6924, 692408, 2008.

Wei-Jhe Tzai et al.; "Metrology of advanced N14 process pattern split at lithography"; Metrology, Inspection, and Process Control for Microlithography XXVIII, edited by Jason P. Cain, Martha I. Sanchez, San Jose, California; Proc. of SPIE vol. 9050, 90502R, 2014.

* cited by examiner

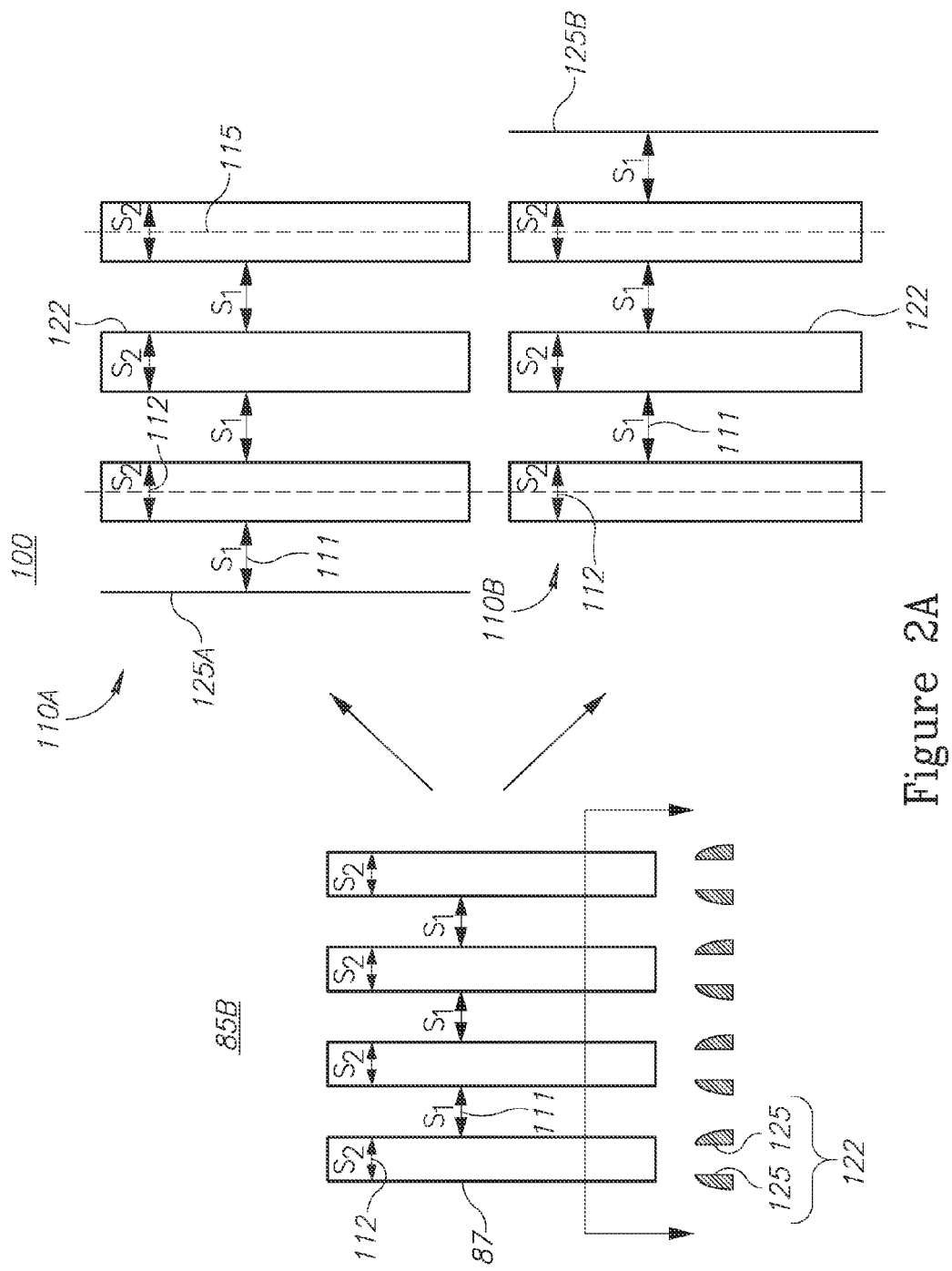

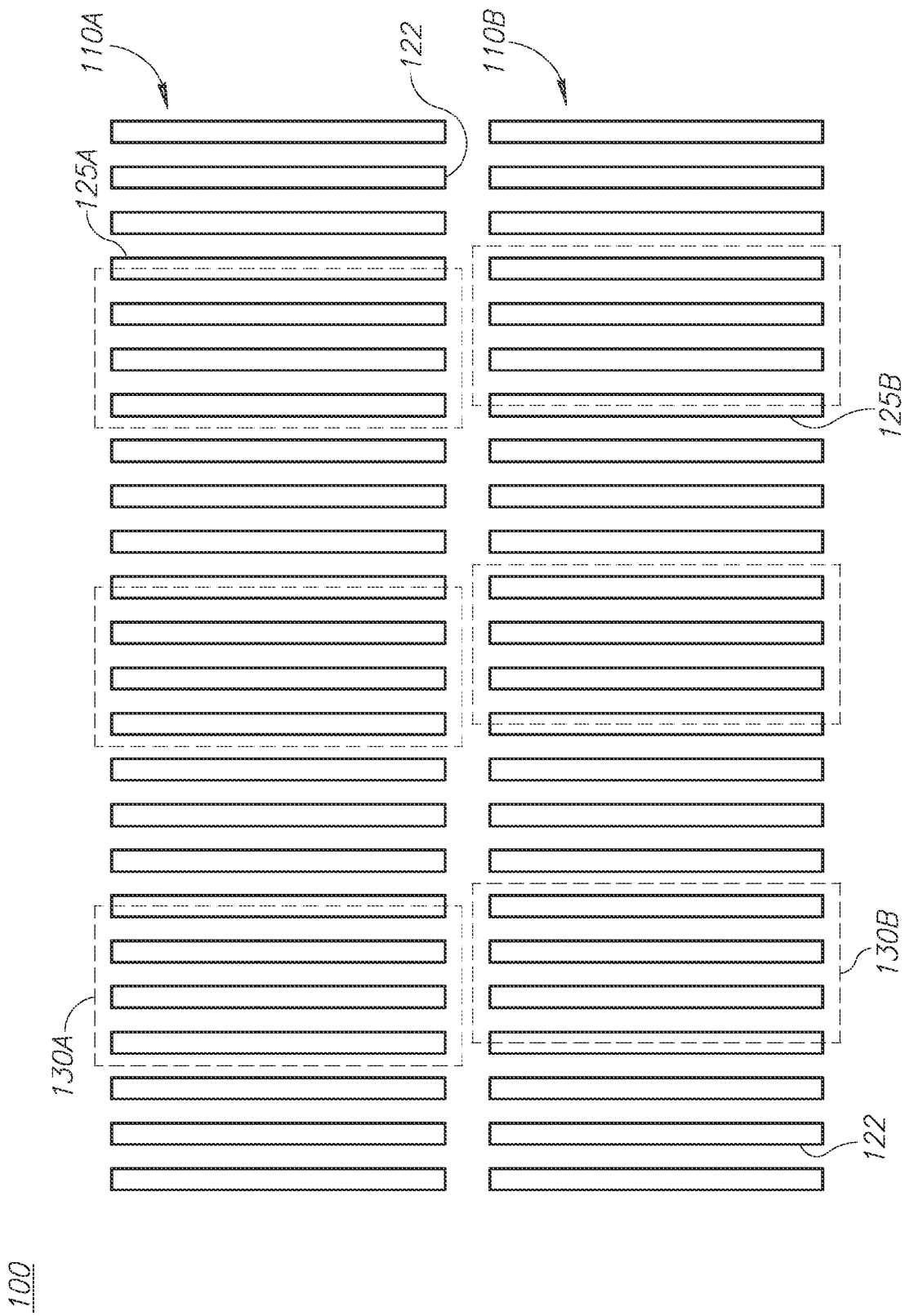

*200*

210 — PRODUCING FIRST AND SECOND MULTIPLY PATTERNED STRUCTURES HAVING, RESPECTIVELY, A SINGLE LEFT-HAND FEATURE OR SPACER AND A SINGLE RIGHT-HAND FEATURE OR SPACER PRODUCED SIMULTANEOUSLY AND SHARING A COMMON PITCH WITH PAIRED FEATURES OR SPACERS IN A MULTIPLY PATTERNED TARGET

220 — ALIGNING THE FIRST AND THE SECOND MULTIPLY PATTERNED STRUCTURES

225 — PRODUCING MULTIPLE CONSECUTIVE FIRST MULTIPLY PATTERNED STRUCTURES WHICH ARE ALIGNED WITH MULTIPLE CONSECUTIVE SECOND MULTIPLY PATTERNED STRUCTURES

230 — PRODUCING MULTIPLE ALTERNATING FIRST AND SECOND MULTIPLY PATTERNED STRUCTURES HAVING A COMMON PITCH

240 — PRODUCING PAIRS OF FIRST AND SECOND MULTIPLY PATTERNED STRUCTURES HAVING A COMMON PITCH, WHEREIN ADJACENT SINGLE FEATURES OR SPACERS ARE UNITED AND ADJACENT RESPECTIVE PAIRED FEATURES OR SPACERS ARE SEPARATED

245 — COMBINING SINGLE LINES INTO SUPERPOSED PERIODIC STRUCTURES HAVING A LARGER PITCH

Figure 6

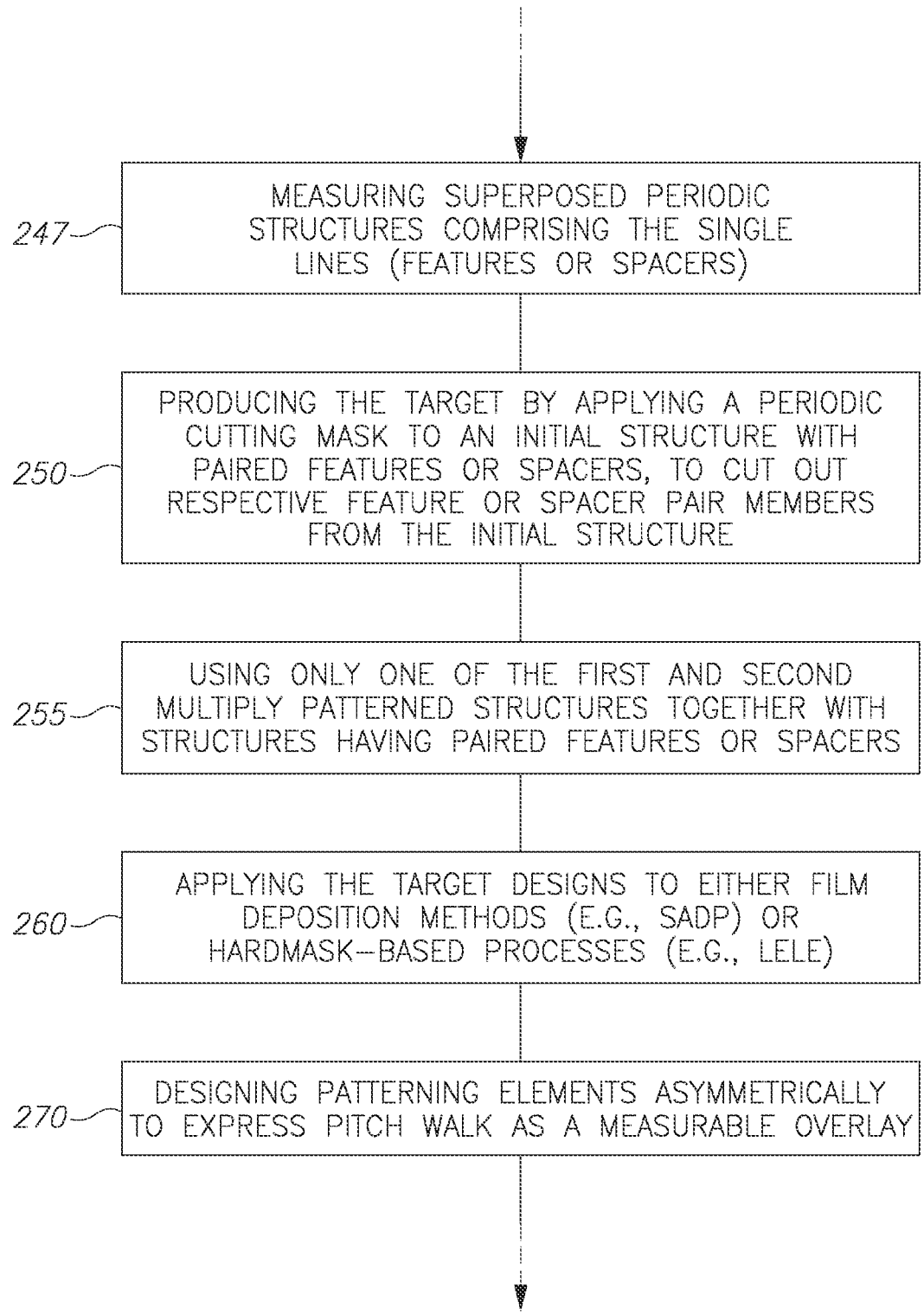
Figure 6 (cont. 1)

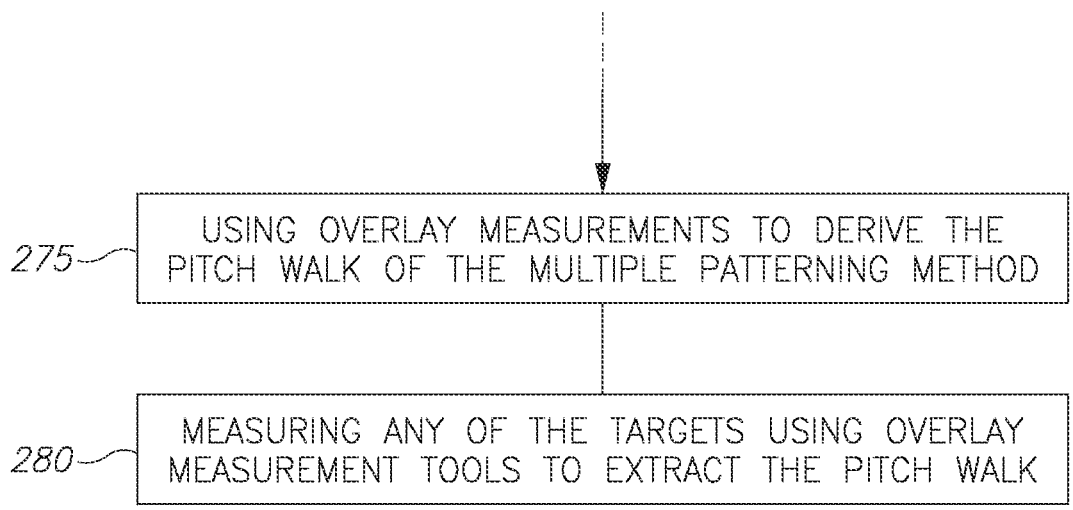
Figure 6 (cont. 2)

OVERLAY MEASUREMENT OF PITCH WALK IN MULTIPLY PATTERNED TARGETS

CROSS REFERENCE TO RELATED APPLICATIONS

This application is filed under 35 U.S.C. § 120 and § 365(c) as a continuation of International Patent Application Ser. No. PCT/US15/11488, filed on Jan. 14, 2015, which application claims the benefit under 35 U.S.C. 119(e) of U.S. Provisional Patent Application No. 61/927,753 filed on Jan. 15, 2014 and United States Provisional Patent Application No. 62/052,877 filed on Sep. 19, 2014, which applications are incorporated herein by reference in their entirety.

FIELD OF THE INVENTION

The present invention relates to the field of metrology, and more particularly, to metrology in multiple patterning.

BACKGROUND OF THE INVENTION

Multiple patterning are lithography techniques that enable reduction of the feature size, such as Self-Aligned Double Patterning (SADP), or in general Self-Aligned Multiple Patterning (SAMP), litho-etch litho-etch (LELE) or in general multiple LE and litho-litho etch (LLE), which have become standard vernacular for near term semiconductor processing. In Self-Aligned Multiple Patterning (SAW), original elements (e.g., linear elements) are split to two or more separate features (e.g., by deposition and etching), termed features or spacers, which are used to produce smaller features using process steps.

However, the splitting methods may incur process variations that might cause "pitch walk", e.g., as a by-product of line critical dimension (CD) and spacer error (in SADP) or overlay variations (in LELE), which affects the later steps, for example, different etched depths due to loading effects. The term "pitch walk" as used herein in this application for SAMP, is defined, in a multiple patterning process, as the difference in spaces between a couple of adjacent features or spacers formed on two sides of the same resist line, versus a couple of adjacent features or spacers formed on two sides of the same space between two adjacent resist lines. For LELE (or LLE) "pitch walk" is the difference in distance between a feature and a feature next to it on its left side vs. a feature next to it on its right side. Currently the main tool for pitch walk measurement is CD-SEM, which is a relatively slow and expensive tool.

BRIEF SUMMARY OF THE INVENTION

One aspect of the present invention provides a multiply patterned metrology target, comprising at least two structures defined by respective pairs of features or spacers, and further comprising: a first multiply patterned structure having a single left-hand features or spacers produced simultaneously and sharing a common pitch with the respective paired features or spacers, and a second multiply patterned structure having a single right-hand features or spacers produced simultaneously and sharing a common pitch with the respective paired features or spacers.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 2A is a high level schematic illustration of a multiply patterned metrology target, according to some embodiments of the invention;

FIG. 3 is a high level schematic illustration of a multiply patterned metrology target having aligned substructures, according to some embodiments of the invention;

DETAILED DESCRIPTION OF THE INVENTION

Figure 1:
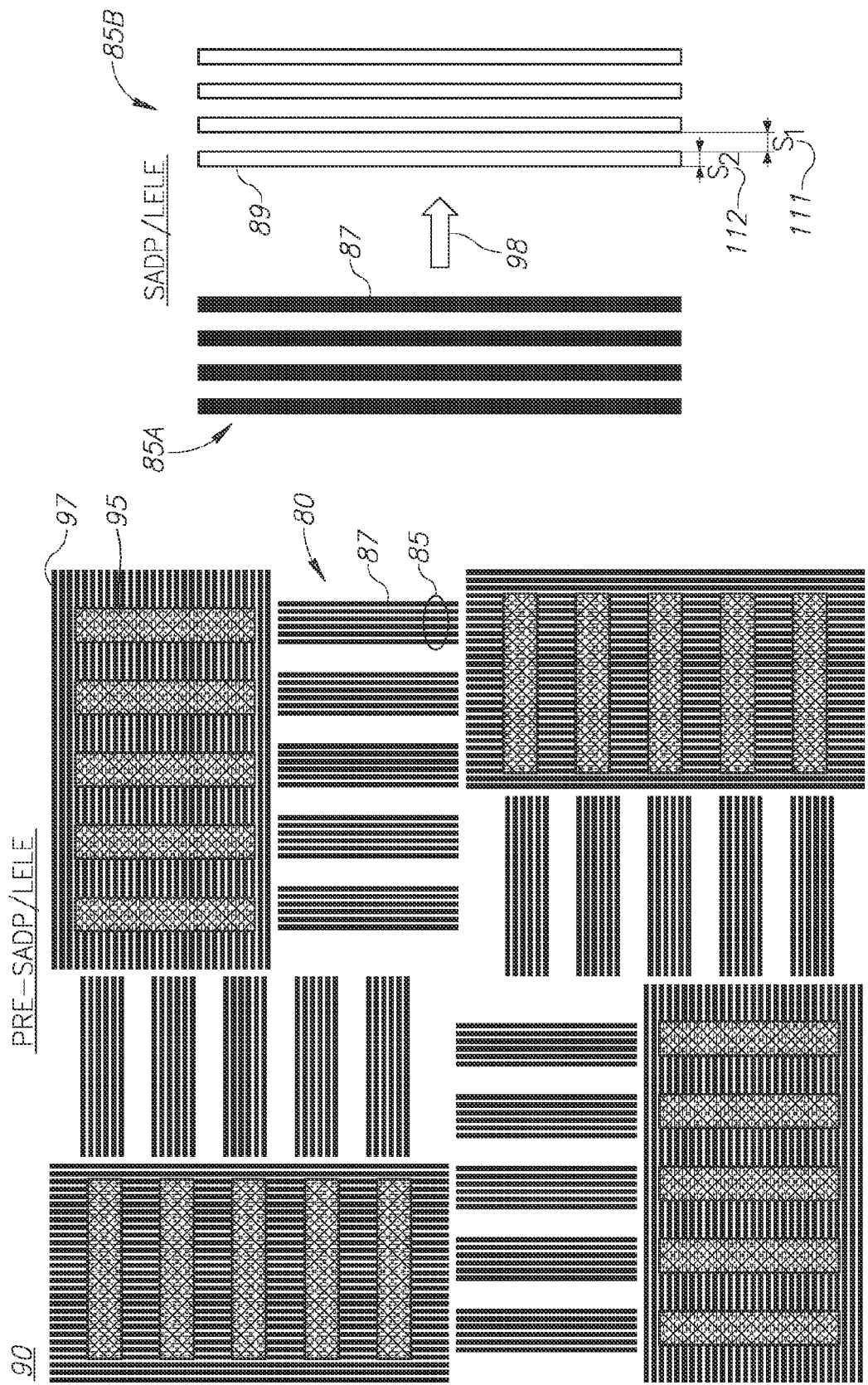
FIG. 1 is a high level schematic illustration of an imaging metrology target onto which self-aligned double patterning (SADP) is applied, according to some embodiments of the invention.

Prior to the detailed description being set forth, it may be helpful to set forth definitions of certain terms that will be used hereinafter. The terms "spacers", "features" and "lines" as used in this application when relating to multiple patterning processes, refer interchangeably to features produced or designed at a higher density than elements of an original design by multiple patterning techniques. Such features comprise spacers in self-aligned patterning technologies which spacer film is deposited on elements of an original design or pattern elements to yield spacers at a higher density than the original) hardmask features as used e.g., in methods employing multiple litho-etch cycles and generally any linear element used repeatedly to increase the spatial frequency and reduce the pitch in multiple patterning techniques. Specifically, it is noted that in the following, the terms "spacer" and "feature" are used interchangeably, e.g., the term "spacers" is also for LELE features, although they are features in hard mask and not the SADP "spacers" produced from a spacer film deposition and etch.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Multiply patterned metrology targets and target design methods are provided to enable pitch walk measurements using overlay measurements. Multiply patterned structures having at least single features or spacers produced simultaneously and sharing a common pitch with the paired features or spacers are used to express pitch walk as a measurable overlay between the structures. For example, targets are provided which comprise a first multiply patterned structure having a single left-hand feature or spacer produced simultaneously and sharing a common pitch with the respective paired features or spacers, and a second multiply patterned structure having a single right-hand feature or spacer produced simultaneously and sharing a common pitch with the respective paired features or spacers. Disclosed solutions are effective for measuring pitch walk in SADP and other multiple patterning processes, which is a key element in process control. For LELE things are similar and more simple: the "left hand side spacer" (or feature) is replaced by the first pattern (LE) and the "right hand side spacer" (or feature) is replaced by the second patterning ($2^{nd}$ LE).

FIG. 1 is a high level schematic illustration of an imaging metrology target 90 onto which double patterning is applied, according to some embodiments of the invention. Double patterning is illustrated as a non-limiting example for multiple patterning, and applied double patterning may be applied e.g., by self-aligned double patterning (SADP) or by a Litho-Etch Litho-Etch (LELE) process as explained above. In a non-limiting manner, target 90 is illustrated as an AIM (Advanced Imaging Metrology) target, yet the design principles disclosed herein may be applied to any type of multiply patterned targets. FIG. 1 shows the pre-patterning design of target 90 having a previous (process) layer 97 illustrated in solid lines and a resist (current) illustrated as hatched elements 95 overlaid on previous layer 97. Target 90 comprises target elements 80 such as bars 85 comprising a periodic pattern of individual elements 87. In multiple patterning processes (e.g., SADP. LELE) each element 87 in a pre-patterning target element 85A is used to produce (98) multiply patterned target elements 85B with pairs of (or multiple) features or spacers 89 (e.g., SADP spacers, LELE, hardmask features or generally lines at higher density) having an internal distance $S_2$ 112 between pair members and an external distance $S_1$ 111 between features or spacer pairs ($S_1+S_2$ being the periodicity pitch of structure 85B derived from elements 85A). Patterning may be applied to any target element, and in general to any section of or whole target 90.

FIG. 2A is a high level schematic illustration of a multiply patterned metrology target 100, according to some embodiments of the invention. In the multiple patterning process, each element 87 is used to produce features or spacers 125, e.g., pairs 122 of features or spacers 125 as illustrated in the cross section on the left side of FIG. 2A (produced e.g., by depositing a film on elements 87 and etching the horizontal parts of the film and possibly elements 87 themselves to leave behind vertical features or spacers 125). Multiply patterned target elements 85B (and/or multiply patterned metrology target 101)) are designed to comprise at least two multiply patterned structures 110A, 110B defined by respective pairs 122 of features or spacers and further comprising a first multiply patterned structure 110A having a single left-hand feature or spacer 125A produced simultaneously and sharing a common pitch with respective paired features or spacers 122, and a second multiply patterned structure 110B having a single right-hand feature or spacer 125 produced simultaneously and sharing a common pitch with respective paired features or spacers 125, both structures 110A, 110B maintaining internal distances $S_2$ 112 between pair members and external distances $S_1$ 111 between feature or spacer pairs 122, and between pairs 122 and single features or spacers 125A, 125B ($S_1+S_2$ being the periodicity pitch common to structures 110A, 110B). Similarly for LELE, $S_1$ is the distance between the first LE to the left feature of the $2^{nd}$ LE and $S_2$ is the respective distance for the right feature.

Figure 2B:
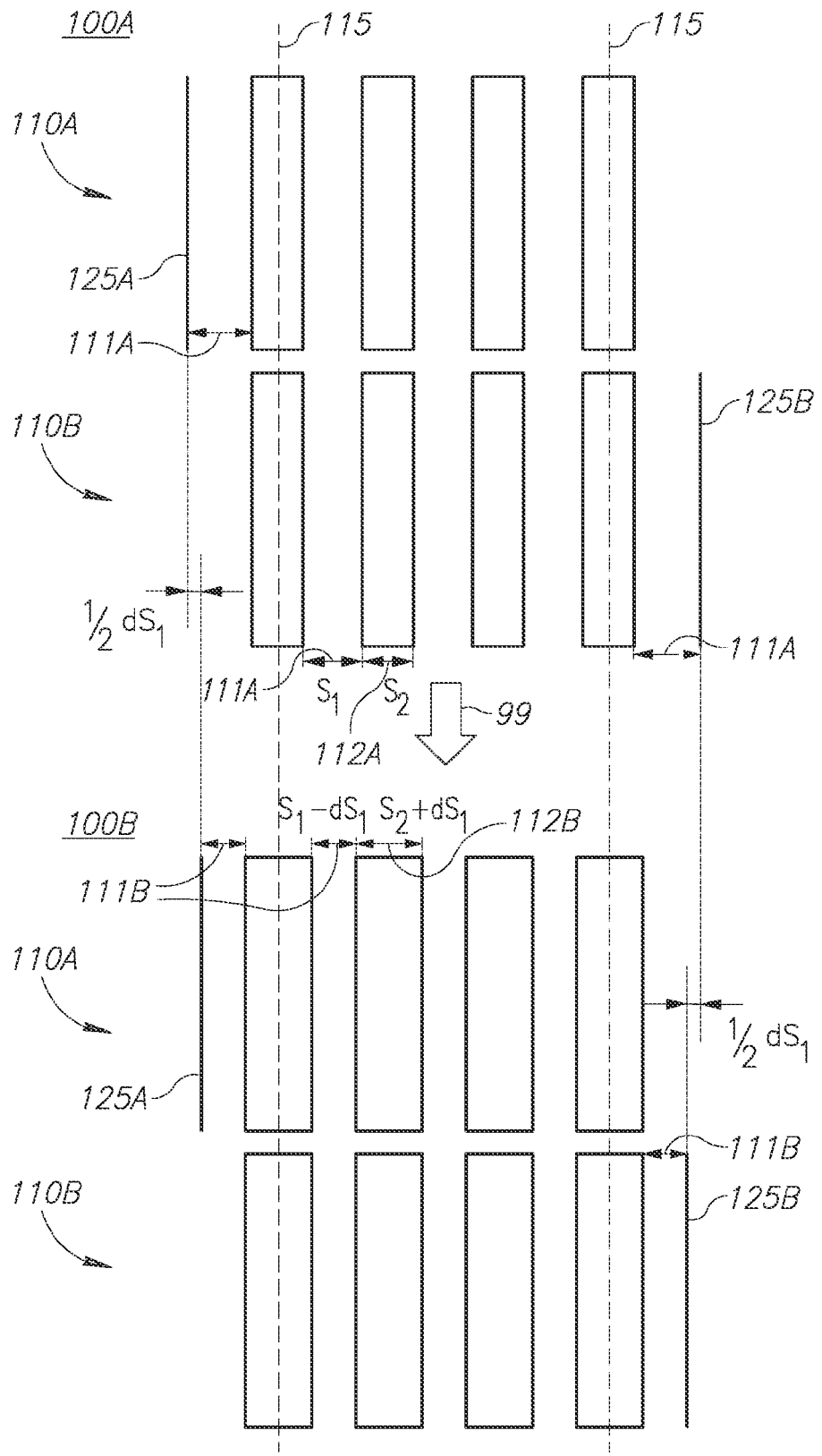
FIG. 2B is a high level schematic illustration of an overlay change due to pitch walk, according to some embodiments of the invention.

FIG. 2B is a high level schematic illustration of an overlay change due to pitch walk 99, according to some embodiments of the invention. FIG. 2B schematically illustrates two target structures 100A, 100B which differ in feature or spacer distances 111A, 112A and 111B, 112B, respectively. The term "pitch walk" 99 designates a change in $S_1$, which may be denoted by $dS_1$. As the structures' segmentation pitch $S_1+S_2$ is constant, any change $dS_1$ in $S_1$ 111 is reflected by a corresponding change $dS_2=-dS_1$ in $S_2$ 112. In certain embodiments, first and second multiply patterned structures 110A, 110B may be aligned as schematically illustrated in FIGS. 2A and 2B by broken alignment lines 115. In case of pitch walk 99 (FIG. 2B), the changes $dS_1$, $dS_2$ are manifested in a change of the relative positions of single left-hand feature or spacer 125A and single right-hand feature or spacer 125B (in $-\frac{1}{2}dS_1$ with respect to lines 115 which represent the structures constant pitch, depending on sign convention), which may be measured as an overlay change using metrology methods such as imaging or scatterometry (e.g., scatterometry overlay metrology SCOL) or other overlay measurement techniques (e.g., micro diffraction based overlay μDBO or imaging with zero order blocking MOS techniques). In target 100B, by way of a non-limiting example, external distances $S_1$ 111B are smaller than external distances $S_1$ 111A in target 100A, namely $S_1(111B)=S_1(111A)-dS_1$ and correspondingly $S_2(112B)=S_2(112A)-dS_1$, as the pitch ($=S_1+S_2$) is constant, as represented by lines 115. Comparing first multiply patterned structures 110A in targets 100A, 100B, respective single left-hand lines 125A are shifted by $-\frac{1}{2}dS_1$ (inwards in target 100B with respect to target 100A), as are respective single right-hand lines 125B in second multiply patterned structures 110B in targets 100A, 100B (inwards in target 100B with respect to target 100A). The inventor has found out that measuring the overlay using structures 110A, 110B is more sensitive and effective than identifying pitch walk in structures composed only of paired features or spacers 122. It is noted that in certain embodiments, one of structures 110A or 110B may be measured with respect to paired features 122 to reveal pitch walk in overlay or asymmetry measurements. Certain embodiments comprise multiply patterned metrology targets 100 comprising at least one multiply patterned structure 110A or 110B, defined by respective pairs of features or spacers 122 and further comprising a multiply patterned structure having a single left-hand or right-hand feature or spacer 125A or 125B respectively, produced simultaneously and sharing a common pitch with the respective paired features or spacers 122.

FIG. 3 is a high level schematic illustration of multiply patterned metrology target 100 having aligned substructures 110A, 110B, according to some embodiments of the invention. FIG. 3 schematically illustrates multiple consecutive first multiply patterned structures 110A which are aligned with multiple consecutive second multiply patterned structures 110B. Furthermore, FIG. 3 schematically illustrates a production method of target 100 from an initial structure of paired features or spacers 125, comprising using a periodic cutting mask 130A, 130B applied to the initial structure to produce the single features or spacers by cutting out respective feature or spacer pair members from the initial structure. Specifically, mask elements 130A are shown to cut away one of paired features or spacers 125 to leave single left-hand features or spacers 125A in first multiply patterned structure 110A and mask elements 130B are shown to cut away one of paired features or spacers 125 to leave single right-hand features or spacers 125B in second multiply patterned structure 110B. As explained for FIGS. 2A, 2B, the alignment of first and second multiply patterned structure 110A, 110B provides for overlay measurements of pitch walk, as it is expressed in relative displacement of single left- and right-hand features or spacers 125A, 125B. The cut layer thus defines single left-hand and single right-hand feature or spacer 125A, 125B respectively, as being on the edge of the measurement bar. Similarly for LELE, cut mask 130A may be used to remove on the right side a line produced by the first LE and used to remove on the left side a line produced by the second LE. For cut mask 130B the LE may switch sides, i.e., makes 130B may be used to remove on the right side a line produced by the second LE and be used to remove on the left side a line produced by the first LE.

In certain embodiments, designs illustrated in FIG. 3 may be measured by imaging metrology to determine pitch walk by overlay measurements of bars comprising multiple consecutive first and second multiply patterned structures 110A, 110B, respectively. In certain embodiments, target designs may be measured by diffraction with one or more previous layers and/or with one or more post layer.

Figure 4:
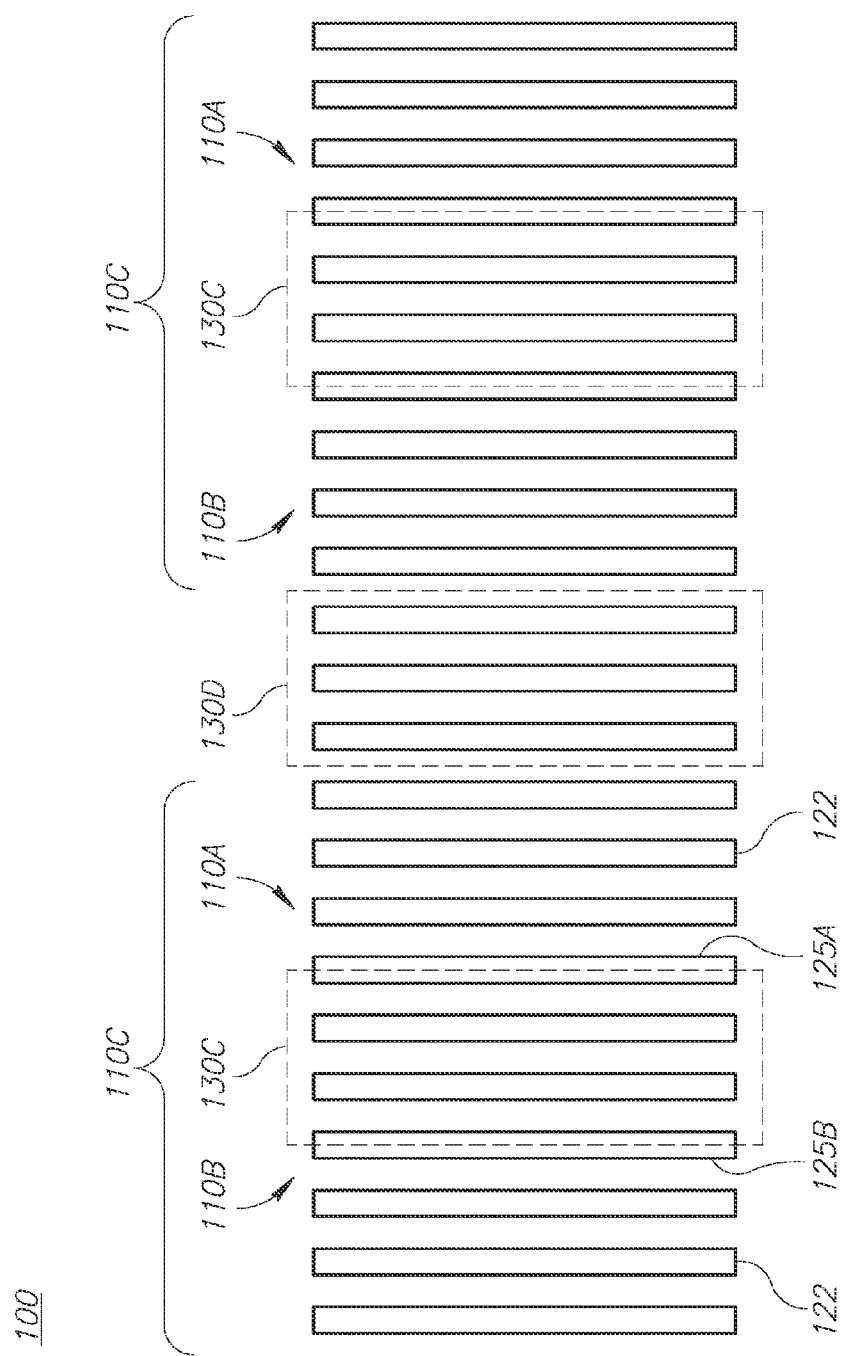
FIG. 4 is a high level schematic illustration of a multiply patterned metrology target having multiple alternating substructures, according to some embodiments of the invention.

FIG. 4 is a high level schematic illustration of multiply patterned metrology target 100 having multiple alternating substructures 110A, 110B, according to some embodiments of the invention. Target 100 may comprise multiple alternating first and second multiply patterned structures 110A, 110B having a common pitch. FIG. 4 schematically illustrates pairs 110C of first and second multiply patterned structures 110A, 110B, which are alternating by using a periodic cutting mask, having cutting mask elements 130C designed to yield opposing single left- and right-hand features or spacers 125A, 125B and cutting mask elements 130D designed to separate pairs 110C of first and second multiply patterned structures 110A, 110B. The production of first and second multiply patterned structures 110A, 110B from an initial structure of pairs 122 of features or spacers ensures pitch uniformity that enable overlay measurements to indicate pitch walk as explained above.

Figure 5:
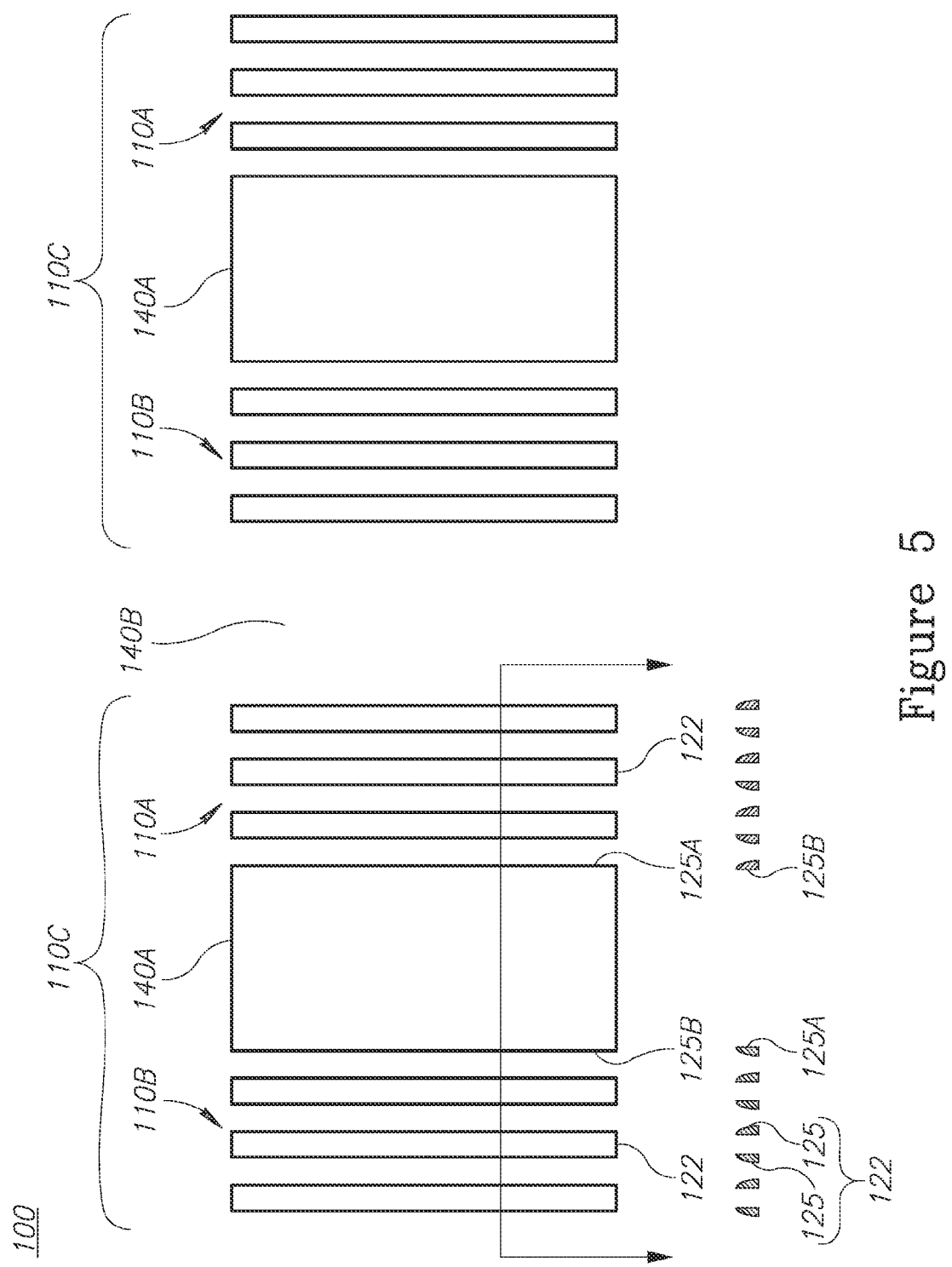
FIG. 5 is a high level schematic illustration of a multiply patterned metrology target having multiple alternating substructures, interspaced by resist blocks and blanks, according to some embodiments of the invention; and, FIG. 6 is a high level schematic flowchart of a method, according to some embodiments of the invention.

In certain embodiments, designs illustrated in FIG. 4 may be measured by scatterometry metrology to determine pitch walk by SCOL signals of combined alternating first and second multiply patterned structures 110A, 110B, respectively, or also by using a previous layer or a post layer to produce together the diffraction FIG. 5 is a high level schematic illustration of multiply patterned metrology target 100 having multiple alternating substructures 110A, 110B, interspaced by resist blocks 140A and blanks 140B, according to some embodiments of the invention. In the multiple patterning process, each element 87 is used to produce features or spacers 125, e.g., pairs 122 of features or spacers 125 as illustrated in the cross section on the left side of FIG. 5. Blocks 140A, which are wider than elements 87, produce features or spacers 125B, 125A which are farther away from each other than features or spacers 125 in pairs 122, and thus provide right-hand and left-hand features or spacers 125B, 125A, respectively. Production of features or spacers 125B, 125A may be carried out similarly to the production of features or spacers 125, e.g., by depositing a film on blocks 140A and etching the horizontal parts of the film and possibly blocks 140A themselves to leave behind vertical features or spacers 125A, 125B.

Target 100 may comprise pairs 110C of first and second multiply patterned structures 110A, 110B. Adjacent single features or spacers (a single right-hand feature or spacer to the left, a single left-hand feature or spacer to the right) may be united into a large resist block 140A (one or more resist features which are wider than feature or spacer pairs 122 and/or wider than the pitch $S_1+S_2$) and adjacent respective paired features or spacers may be separated by a large (resist) blank 140B. The edges of resist block 140A thus function as single left-hand and right-hand features or spacers 125A, 125B. For example, large resist block 140A may have a width of an integer number of pitch values plus one internal distance $S_2$, namely $n \cdot p + S_2$ and large blank 140B may have a width of an integer number of pitch values plus one external distance S namely $n \cdot p + S_1$ with n being an integer and p being the pitch $p = S_1 + S_2$ (block 140A and blank 140B may be designed to replace cutting mask elements 130C, 130D shown in FIG. 4, respectively). Designs illustrated in FIG. 5 may be measured by scatterometry metrology to determine pitch walk by SCOL signals of combined alternating first and second multiply patterned structures 110A, 110B, respectively, or also by using a previous layer or a post layer.

Certain embodiments comprise periodic cutting masks applied to an initial structure with paired features or spacers, wherein the single features or spacers are produced by cutting out respective feature or spacer pair members from the initial structure. Certain embodiments comprise target design files of targets 100.

Certain embodiments comprise overlay metrology measurements of any of targets 100, extracting a pitch walk of patterned structure(s) 110 from the measured overlay.

FIG. 6 is a high level schematic flowchart of a method 200, according to some embodiments of the invention. Method 200 may comprise designing any of the embodiments targets 100 and producing respective target design files, e.g., carried out at least partially by a computer processor. Method 200 may further comprise measuring signals such as overlay signals from any of the embodiments of targets 100, e.g., using imaging and/or scatterometry metrology. Certain embodiments of the invention comprise the measured metrology signals of any of targets 100.

Method 200 comprises producing, in a multiply patterned metrology target having pairs of features or spacers, a first multiply patterned structure having a single left-hand feature or spacer produced simultaneously and sharing a common pitch with the pairs of features or spacers, and a second multiply patterned structure having a single right-hand feature or spacer produced simultaneously and sharing a common pitch with the pairs of features or spacers (stage 210).

Method 200 may further comprise producing the target by applying a periodic cutting mask to an initial structure with paired features or spacers, to cut out respective feature or spacer pair members from the initial structure (stage 250).

Method 200 may further comprise aligning the first and the second multiply patterned structures (stage 220) and possibly producing multiple consecutive first multiply patterned structures which are aligned with multiple consecutive second multiply patterned structures (stage 225).

Method 200 may further comprise producing multiple alternating first and second multiply patterned structures having a common pitch (stage 230).

Method 200 may comprise producing pairs of first and second multiply patterned structures having a common pitch, with adjacent single features or spacers being united and adjacent respective paired features or spacers being separated (stage 240). In certain embodiments, method 200 may comprise combining single lines (i.e., features or spacers) into superposed periodic structures having a larger pitch (stage 245) and/or measuring superposed periodic structures comprising the single lines (features or spacers) (stage 247).

Method 200 may comprise producing the target by applying a periodic cutting mask to an initial structure with paired features or spacers, to cut out respective feature or spacer pair members from the initial structure (stage 250). In certain embodiments, method 200 may comprise using only one of the first and second multiply patterned structures together with structures having paired features or spacers (stage 255).

Method 200 may comprise applying the target designs to either film deposition methods (e.g., SADP) or hardmask-based processes (e.g., LELE) (stage 260).

In certain embodiments, method 200 may comprise designing patterning elements asymmetrically to express pitch walk as measurable overlay (stage 270). Method 200 may further comprise using overlay measurements (e.g., imaging, scatterometry) to derive the pitch walk of the multiple patterning method (stage 275) and/or measuring any of the targets using overlay measurement tools to extract the pitch walk (stage 280).

It is noted that certain embodiments comprise designs of targets 100 and methods 200 for multiple patterning with respective multiple feature or spacer pairs, e.g., triple patterning, quadruple patterning etc., which are carried out according to the disclosed principles. Multiply patterned targets may be modified to leave single features or spacers out of feature or spacer pairs which transform pitch walk into a measurable overlay, which is measured by overlay metrology techniques. It is noted, that in multiple (>2) patterning, there are several potential "pitch walk" effects which may be measured by respective asymmetric structures 110 produced at several processing steps. For example, in SAMP, the resulting complex structures may be measured according to similar principles, measuring respective left-hand and/or right-hand features or spacers at corresponding patterning steps. Structures 110 at each step may be measured and the shifts in respective steps may be measured as respective pitch walks using overlay measurement techniques, i.e., a first pitch walk may be measured and additional pitch walks may be measured later, when producing more features by patterning. Pitch walk measurements in consecutive LE steps may be measured consecutively along using the same design, production and measurement principles.

It is explicitly noted that disclosed designs of targets 100 and methods 200 are applicable to features etched in hard mask (rather than deposited film spacers) produced by the LELE (Litho-Etch-Litho-Etch) techniques or by any other technique, as well as to SADP apcers. Similarly, pitch walk structures may be produced and may be measured for multiple pattering of LELELE or LELELELE etc. (generally marked $(LE)_n$, with n≥2) by the method described for SADP as an example.

Overlay measurements used to extract pitch walk(s) from the measured overlay(s) are part of the present disclosure as embodiments of the disclosed structures and targets uniquely enable pitch walk measurements using measured overlays to enhance and improve the accuracy and metrology of multiple patterned structures.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology target, comprising:
    a first structure formed from a multiple-patterning process including a first patterning process and a second patterning process, the first structure including one or more feature pairs, wherein a given feature pair of the one or more feature pairs includes a first pair element and a second pair element on a common layer separated by a first pitch, wherein the first structure further includes an isolated first pair element on the common layer formed in a common process with the one or more feature pairs, wherein elements of adjacent feature pairs of the one or more feature pairs are separated by a second pitch equal to the first pitch, wherein the isolated first pair element is separated from an adjacent element of the one or more feature pairs by the second pitch; and
    a second structure formed from the multiple-patterning process, the second structure including one or more additional feature pairs, wherein the second structure further includes an isolated second pair element formed in a common process with the one or more additional feature pairs, wherein elements of adjacent feature pairs of the one or more additional feature pairs are separated by the second pitch, wherein the unpaired second pair element is separated from an adjacent element of the one or more additional feature pairs by the second pitch, wherein the one or more feature pairs and the one or more additional feature pairs are formed by the first patterning process generating two or more pre-pattern elements and the second patterning process defining the first pitch based on the two or more pre-pattern elements, wherein an overlay metrology measurement of the first structure and the second structure is indicative of one or more errors in the multiple-patterning process manifested as a deviation of the first pitch with respect to the second pitch.

2. The target of claim 1, wherein the one or more feature pairs of the first structure are distributed along a first direction, wherein the one or more additional feature pairs of the second structure are distributed along the first direction, wherein the one or more feature pairs of the first structure and the one or more additional feature pairs of the second structure are aligned along a second direction perpendicular to the first second direction.

3. The target of claim 1, further comprising:
multiple consecutive first structures which are aligned with multiple consecutive second structures.

4. The target of claim 1, further comprising:
multiple alternating first and second structures.

5. The target of claim 1, wherein at least one of the unpaired first pair element or the unpaired second pair element are produced using a cutting mask applied to a pre-pattern element of the two or more pre-patterned elements.

6. The target of claim 1, further comprising:
a previous patterned layer or a post patterned layer.

7. The target of claim 1, wherein the multiple-patterning process includes three or more patterning processes.

8. The target of claim 1, wherein the one or more errors in the multiple-patterning process comprise:
a pitch walk.

9. The target of claim 1, wherein the multiple-patterning process comprises:
at least one of a self-aligned double patterning process, a self-aligned multiple patterning process, a double hardmask patterning process, or a multiple hardmask patterning process.

10. A metrology target, comprising:
a first structure formed from a multiple-patterning process including a first patterning process and a second patterning process, the first structure including one or more feature pairs, wherein a given feature pair of the one or more feature pairs includes a first pair element and a second pair element on a common layer separated by a first pitch, wherein the first structure further includes a first pair element of a separator feature pair on the common layer formed in a common process with the one or more feature pairs, wherein elements of adjacent feature pairs of the one or more feature pairs are separated by a second pitch equal to the first pitch, wherein the first feature element of the separator feature pair is separated from an adjacent element of the one or more feature pairs by the second pitch; and
a second structure formed from the multiple-patterning process, the second structure including one or more additional feature pairs, wherein the second structure further includes a second pair element of the separator feature pair, wherein the first and second pair elements of the separator feature pair are separated by a third pitch larger than the second pitch, wherein elements of adjacent feature pairs of the one or more additional feature pairs are separated by the second pitch, wherein the second pair element of the separator feature pair is separated from an adjacent element of the one or more feature pairs by the second pitch, wherein the one or more feature pairs, the separator feature pair, and the one or more additional feature pairs are formed by the first patterning process generating three or more pre-pattern elements and the second patterning process defining the first pitch and the third pitch based on the three or more pre-pattern elements, wherein an overlay metrology measurement of the metrology target is indicative of one or more errors in the multiple-patterning process manifested as a deviation of the first pitch with respect to the second pitch.

11. The target of claim 10, further comprising:
a previous patterned layer or a post patterned layer.

12. The target of claim 10, wherein the multiple-patterning process includes three or more patterning processes.

13. The target of claim 10, wherein the one or more errors in the multiple-patterning process comprise:
a pitch walk.

14. The target of claim 10, wherein the multiple-patterning process comprises:
at least one of a self-aligned double patterning process, a self-aligned multiple patterning process, a double hardmask patterning process, or a multiple hardmask patterning process.

15. A method comprising:
fabricating, with a first patterning process of a multiple-patterning process, two or more pre-pattern elements on a common layer associated with a first metrology structure;
fabricating, with the first patterning process, two or more pre-pattern elements on the common layer associated with a second metrology structure;
fabricating, with a second patterning process of the multiple-patterning process, one or more feature pairs defined by at least one of the pre-pattern elements associated with the first metrology structure, wherein a given feature pair of the first metrology structure includes a first pair element and a second pair element separated by a first pitch, wherein elements of adjacent feature pairs of the first metrology structure are separated by a second pitch different than the first pitch;
fabricating, with the second patterning process, an isolated first pair element defined by one of the pre-pattern elements associated with the first metrology structure;
fabricating, with the second patterning process, one or more feature pairs defined by at least one of the pre-pattern elements associated with the second metrology structure, wherein a given feature pair of the second metrology structure includes a first pair element and a second pair element separated by the first pitch, wherein elements of adjacent feature pairs of the first metrology structure are separated by the second pitch;
fabricating, with the second patterning process, an isolated second pair element defined by one of the two or more pre-pattern elements associated with the second metrology structure; and
performing an overlay metrology measurement of the first metrology structure and the second metrology structure to determine one or more errors in the multiple-patterning process based on a deviation of the first pitch with respect to the second pitch.

16. The method of claim 15, wherein fabricating, with the second patterning process, an isolated first pair element defined by one of the pre-pattern elements of the first metrology structure comprises:

applying a cutting mask to the one of the pre-pattern elements of the first metrology structure during the second patterning process.

17. The method of claim 15, further comprising:

aligning the first metrology structure and the second metrology structure.

18. The method of claim 15, further comprising:

producing multiple consecutive first metrology structures which are aligned with multiple consecutive second metrology structures.

19. The method of claim 15, further comprising:

producing multiple alternating first metrology structures and second metrology structures.

20. The method of claim 15, wherein the multiple-patterning process comprises:

at least one of a self-aligned double patterning process, a self-aligned multiple patterning process, a double hardmask patterning process, or a multiple hardmask patterning process.

21. The method of claim 15, wherein the one or more errors in the multiple-patterning process comprise:

a pitch walk.

22. The method of claim 15, wherein fabricating, with the second patterning process, an isolated second pair element defined by one of the pre-pattern elements of the second metrology structure comprises:

applying a cutting mask to the one of the pre-pattern elements of the second metrology structure during the second patterning process.

* * * * *